United States Patent [19]

Dousse et al.

[11] 4,235,818
[45] Nov. 25, 1980

[54] PROCESS FOR PRODUCING ALPHA-MONOCHLOROACETOACETIC ACID MONOMETHYLAMIDE

[75] Inventors: Roland Dousse; Ernst Kägi, both of Monthey, Switzerland

[73] Assignee: Ciba-Geigy Corporation, Ardsley, N.Y.

[21] Appl. No.: 963,057

[22] Filed: Nov. 22, 1978

Related U.S. Application Data

[63] Continuation-in-part of Ser. No. 811,662, Jun. 30, 1977, abandoned.

[51] Int. Cl.² .................... C07C 103/34; C07C 97/02
[52] U.S. Cl. .................................................. 564/199
[58] Field of Search ...................... 260/561 K, 561 HL

[56] References Cited

U.S. PATENT DOCUMENTS

| | | | |
|---|---|---|---|
| 3,258,394 | 6/1966 | Hall et al. | 424/211 |
| 3,284,500 | 11/1966 | Tieman | 260/561 K |
| 3,449,421 | 6/1969 | Pearson | 260/561 K |
| 3,483,252 | 12/1969 | Beriger | 260/561 K |
| 3,917,694 | 11/1975 | Reinink | 260/561 K |

FOREIGN PATENT DOCUMENTS 2065067  6/1971  France ................. 260/561 K

*Primary Examiner*—Arthur P. Demers
*Attorney, Agent, or Firm*—Karl F. Jorda

[57] ABSTRACT

A process for the production of α-monochloroacetoacetic acid monomethylamide is disclosed which comprises chlorinating acetoacetic acid monomethylamide in the presence of urea and a water-soluble alkali metal salt or ammonium salt at a temperature of between −20° and +10° C. with 80–95% of the equivalent amount of chlorine; neutralizing the reaction mixture; separating the precipitated α-monochloroacetoacetic acid monomethylamide; and partially recycling the mother liquor back into the chlorination process. α-Chloroacetoacetic acid monomethylamide is a valuable intermediate for producing insecticidal active compounds, for example dimethyl-1-methyl-2-(methylcarbamoyl)-vinyl phosphate.

11 Claims, No Drawings

PROCESS FOR PRODUCING ALPHA-MONOCHLOROACETOACETIC ACID MONOMETHYLAMIDE

CROSS-REFERENCE TO RELATED APPLICATION

This application is a continuation-in-part of application, Ser. No. 811,662, filed June 30, 1977, now abandoned.

The present invention relates to a process for producing α-monochloroacetoacetic acid monomethylamide by the reaction of chlorine with an aqueous solution of acetoacetic acid monomethylamide in the presence of urea.

α-Chloroacetoacetic acid monomethylamide is a valuable intermediate for producing insecticidal active ingredients. A representative of this class of compounds, namely dimethyl-1-methyl-2-(methylcarbamoyl)-vinyl phosphate, and also the production and use thereof are described in the U.S. Pat. No. 3,258,394.

The production of pure α-monochloroacetoacetic acid monomethylamide by chlorination of acetoacetic acid monomethyl amide is difficult in practice because on reaction of chlorinating agents, particularly sulfuryl chloride and chlorine, there is formed, in consequence of the high reactivity of the 2-methylene group, besides the monochlorinated product desired, always the dichlorinated product. In order to prevent this undesirable secondary reaction, it has already been suggested to use as starting materials, instead of acetoacetic acid monomethylamide, derivatives thereof, for example the ethylene ketal (see German Patent Specification No. 1,247,294) or the α-(α'-hydroxy-β',β',β'-trichloroethyl)-acetoacetic acid monomethylamide (see U.S. Pat. No. 3,458,573) obtainable by reaction of acetoacetic acid monomethylamide with chloral; and to split off after chlorination the introduced protective groups. This process however requires additional reaction steps for the introduction and splitting-off of the protective group concerned and is therefore complicated.

It has further been suggested to perform the chlorination of acetoacetic acid amides, inter alia also of acetoacetic acid monoalkylamides, by a process, described in the U.S. Pat. No. 3,284,500, with sulfuryl chloride in the presence of a halogenated aliphatic hydrocarbon. This process yields however only in a very high dilution satisfactory results. Thus, for example, on chlorination of acetoacetic acid dimethylamide in methylene chloride with a volume ratio of solvent to acetoacetic acid dimethylamide of 5:1, there is obtained besides 92% of α-monochloroacetoacetic acid dimethylamide also 8% of α,α-dichloroacetoacetic acid dimethylamide. With the chlorination of acetoacetic acid monoalkylamides, this ratio of monochlorinated product to dichlorinated product is even more unfavourable. Therefore this process too is unsatisfactory, with regard both to the handling of large amounts of solvent and to the attainable result. A further disadvantage of this process is that sulfur dioxide is formed as by-product.

According to a further known process, described in the U.S. Pat. No. 3,483,252, α-chloroacetoacetic acid monomethylamide is produced by reaction of chlorine with an aqueous solution of acetoacetic acid monomethylamide at temperatures below 0° C. in the presence of urea and an organic solvent miscible with water. The product obtained by this process consists to the extent of 90% of α-monochloroacetoacetic acid monomethylamide which contains, besides other impurities, 5% of α,α-dichloroacetoacetic acid monomethylamide. The yield of pure α-monochloroacetoacetic acid monomethylamide is 78.2% of theory. With regard to the yield attainable and the purity of the end product, this process too is not able to produce satisfactory results.

The object of the present invention is therefore to provide a process which renders possible the production of α-chloroacetoacetic acid monomethylamide in a simple manner and with a satisfactory yield and degree of purity.

This is achieved according to the present invention by a process comprising performing the chlorination of acetoacetic acid monomethylamide in the presence of a water-soluble alkali metal salt or ammonium salt at a temperature of between −20 and +10° C. with 80 to 95% of the equivalent amount of chlorine; neutralising the reaction mixture; separating the precipitated α-chloroacetoacetic acid monomethylamide; and partially recycling the mother liquor back into the chlorination stage.

The chlorination of acetoacetic acid monomethylamide according to the invention is performed in the presence of 0.3 to 0.1 mole, preferably 0.6 to 0.8 mole, of urea per mole of acetoacetic acid monomethylamide.

Suitable water-soluble alkali metal salts and ammonium salts are those which are inert to chlorine, particularly chlorides and sulfates. Examples of suitable water-soluble alkali metal salts and ammonium salts are sodium chloride, sodium sulfate, potassium chloride, potassium sulfate, ammonium chloride and ammonium sulfate. Preferred salts amongst these are sodium chloride and ammonium chloride.

It is advantageous to add to the reaction mixture an organic water-immiscible solvent which prevents the reaction mixture forming foam and crusts on the wall of the reaction vessel. Such solvents which have proved satisfactory for this purpose are especially halogenated hydrocarbons, such as 1,2-dichloroethane, 1,1-dichloroethane, chloroform, carbon tetrachloride or methylene chloride. A particularly suitable solvent is 1,2-dichloroethane. The forming of foam and crusts by the reaction mixture is prevented by adding these solvents in amounts of 1 to 2 per cent by weight, relative to the total amount of reaction mixture.

For carrying out the process according to the invention, it is advantageous to use a reaction mixture containing 45 to 65% by weight of water, 15 to 25% by weight, preferably 18 to 20% by weight, of acetoacetic acid monomethylamide, 8 to 20% by weight of a water-soluble alkali metal salt or ammonium salt, 8 to 10% by weight of urea and 1 to 2% by weight of one of the aforementioned organic water-immiscible solvents, preferably 1,2-dichloroethane.

The chlorination of acetoacetic acid monomethylamide, according to the invention, is performed at temperatures of between −20° and +10° C. The amount of chlorine to be used depends on the chlorination temperature in the sense that, within the aforegiven range, there is used at the lower temperatures 95% of the equivalent amount of chlorine relative to the acetoacetic acid monomethylamide, and at the higher temperatures 90% of the equivalent amount of chlorine relative to the acetoacetic acid monomethylamide. For obtaining a high quality of end product it is advantageous at temperatures of 0° C. and above to further reduce the amount of chlorine and to use, for example, 85 to 90% of the equivalent amount of chlorine relative to acetoacetic acid monomethylamide.

After completion of chlorination, the reaction mixture is neutralised by the addition of an aqueous alkali metal hydroxide solution, for example 50% sodium hydroxide solution, or preferably by the introduction of ammonia. The α-monochloroacetoacetic acid monomethylamide which has precipitated from the reaction mixture is subsequently separated by filtration or by centrifuging. The product obtained in this way can after drying be further used directly. It is however also possible to dissolve the moist product, obtained after filtration or centrifuging, in an organic solvent immiscible with water, to separate the water, and to obtain the product by evaporation of the solvent. Suitable solvents for this purpose are in particular those halogenated hydrocarbons which are added to the reaction mixture to prevent the formation of foam and crusts.

After separation of the α-monochloroacetoacetic acid monomethylamide, 50 to 85% of the mother liquor obtained is fed back into the chlorination process. The acetoacetic acid monomethylamide consumed by reaction, and also the auxiliaries and additives lost by partial removal of the mother liquor, are replenished in such a way that there is again available a starting mixture of the aforementioned composition.

The process according to the invention can be performed both continuously and discontinuously. It is particularly suitable for continuous operation. The continuous method of performing the process is especially advantageous because it is possible in this case to operate with short chlorination times of 5 to 30 minutes, whereas the chlorination time with the discontinous performance of the process is about 1–3 hours.

It is possible with the process according to the invention to produce α-monochloroacetoacetic acid monomethylamide, in satisfactory yield and purity, by direct reaction of chlorine with acetoacetic acid monomethylamide with the sole use of water as solvent. The process can be carried out both continuously and discontinuously in a simple manner and at low cost since the employed auxiliaries are all cheap and readily available. The yields attainable with the process according to the invention are 85 to 88% of theory. The product obtained is 93 to 98% pure. In comparison, a yield of 86.9% of theory and a 90% pure product are obtained by the process disclosed in the U.S. Pat. No. 3,483,252. Compared with the process described in the U.S. Pat. No. 3,483,252, the process according to the present invention has the further advantage that it can be performed at higher temperatures, in consequence of which the expenditure on apparatus and the energy requirement are considerably reduced.

The process according to the invention is further illustrated by the following Examples.

EXAMPLE 1

The reaction vessel is a double-cased tube reaction vessel made from Hastelloy C with an internal diameter of 200 mm, which is provided with a hollow inner stirrer having the same length as the reaction vessel and a diameter of 160 mm. The stirrer is fitted with a row of scrapers in order to prevent the formation of a crust of precipitated reaction product on the wall of the vessel. The wall of the reaction vessel and the stirrer are cooled with brine. Along the wall of the reaction vessel are mounted at regular intervals thermocouples to provide temperature control. On the floor of the reaction vessel are located an opening for the introduction of the chlorination solution, and two inlets for chlorine gas, one of which is situated on the bottom and the other about half way up the wall of the reaction vessel.

Into this reaction vessel is fed per hour 64 kg of a chlorination solution, cooled to $-5°$ C., composed of 59.0% by weight of water, 21.0% by weight of acetoacetic acid monomethylamide, 10.0% by weight of sodium chloride, 8.5% by weight of urea and 1.5% by weight of 1,2-dichloroethane; and simultaneously there is introduced through the chlorine inlets, 50% through the bottom inlet and 50% through the wall inlet, 7.86 kg (110.9 moles) of chlorine. A temperature of $-10°\pm2°$ C. is maintained in the reaction vessel during the addition of chlorine. The acid suspension of α-monochloroacetoacetic acid monomethylamide issuing from the upper part of the reaction vessel is stored for about 10 minutes in a buffer vessel and is subsequently neutralised in a stirrer vessel at $-5°$ to $0°$ C., by the introduction of ammonia, to a pH value of 6 to 6.5. The suspension is then centrifuged and the moist product, 13.4 kg, is dissolved at $35°$ to $40°$ C. in double the amount of 1,2-dichloroethane. After separation of the aqueous phase, there is distilled off from the organic phase, under reduced pressure at $75°$ to $80°$ C., firstly the dissolved water and then the 1,2-dichloroethane. The residue, crystallising on cooling (12.1 kg/h), consists to the extent of 96% (11.61 kg/h; 70% of theory relative to the employed chlorine) of α-monochloroacetoacetic acid monomethylamide.

EXAMPLE 2

Into the same reaction vessel is fed per hour 64 kg of a chlorination solution, cooled to $-5°$ C., composed of 59.0% by weight of water, 21.0% by weight of acetoacetic acid monomethylamide (=116.7 moles), 10.0% by weight of sodium chloride, 8.5% by weight of urea and 1.5% by weight of 1,2-dichloroethane; and simultaneously there is introduced through the chlorine inlets, 50% through the bottom inlet and 50% through the wall inlet, 6.62 kg (93.4 moles) of chlorine (=80% of the theoretical amount). A temperature of $-5°$ C. is maintained in the reaction vessel during the addition of chlorine. The acid suspension of α-monochloroacetoacetic acid monomethylamide issuing from the upper part of the reaction vessel is stored for about 10 minutes in a buffer vessel and is subsequently neutralised in a stirrer vessel at $-5°$ to $0°$ C., by the introduction of ammonia (1.6 kg), to a pH value of 6 to 6.5. The suspension is then centrifuged and the moist product, 10.2 kg, is dissolved at 35 to $40°$ C. in double the amount of 1,2-dichloroethane. After separation of the aqueous phase, there is distilled off from the organic phase, under reduced pressure at 75 to $80°$ C., firstly the dissolved water and then the 1,2-dichloroethane. The residue, crystallising on cooling (9.48 kg/h), consists to the extent of 96% (9.10 kg/H; 65.1% of theory relative to the employed chlorine) of α-monochloroacetoacetic acid monomethylamide.

EXAMPLE 3

From 80% of the mother liquor obtained according to Example 2 containing 3.3 kg α-monochloroacetoacetic acid monomethylamide and 2.2 kg acetoacetic acid monomethylamide there is prepared, by the addition of water, solid acetoacetic acid monomethylamide, urea, sodium chloride and 1,2-dichloroethane, a fresh chlorination solution containing 46.3% by weight of water, 19.1% by weight of acetoacetic acid monomethylamide, 6.7% by weight of α-monochloroacetoacetic acid monomethylamide, 8.1% by weight of urea, 8.8% by weight of sodium chloride, 1.4% by weight of 1,2-dichloroethane and 6.1% by weight of ammonium chloride. There is chlorinated and neutralised per hour in each case 64 kg of this solution (12.22 kg of acetoacetic acid monomethylamide per hour (=106.17 moles) with the use of 95% of the equivalent amount of chlorine (=100.8 moles=7.15 kg), using the method described in Example 1. Obtained per hour is 18.70 kg of the product consisting of 13.89 kg of 95% α-monochloroacetoacetic acid monomethylamide, 3.0 kg of a mixture of ammonium chloride and sodium chloride and 1.81 kg of mother liquor. The moist product is treated at 35°–40° C. with 28 kg of 1,2-dichloroethane, and the insoluble mixture of ammonium chloride and sodium chloride is separated by filtration. From this salt mixture it is possible to regenerate ammonia, in a simple manner, by the addition of sodium hydroxide solution. The aqueous phase is separated from the filtrate, and from the organic phase are subsequently distilled off, under reduced pressure at 75°–80° C., firstly the dissolved water and then 1,2-dichloroethane. There is obtained per hour 13.89 kg of 95% α-monochloroacetoacetic acid monomethylamide, which corresponds to a nett yield of α-monochloroacetoacetic acid monomethylamide of 13.20 kg per hour (87.5% of theory).

We claim:

1. In a process for producing α-monochloroacetoacetic acid monomethylamide by reaction of chlorine with an aqueous solution of acetoacetic acid monomethylamide in the presence of urea at a low temperature, the improvement which comprises performing the chlorination of acetoacetic acid monomethylamide in the presence of a water-soluble alkali metal salt or ammonium salt at a temperature of between −20 and +10° C. with 80–95% of the equivalent amount of chlorine; neutralising the reaction mixture; separating the precipitated α-monochloroacetoacetic acid monomethylamide; and partially recycling the mother liquor back into the chlorination process.

2. Process according to claim 1, wherein the water-soluble alkali metal salts and ammonium salts used are sodium chloride, sodium sulfate, potassium chloride, potassium sulfate, ammonium chloride and ammonium sulfate.

3. Process according to claim 1, wherein the water-soluble alkali metal salts and ammonium salts used are sodium chloride or ammonium chloride.

4. Process according to claim 1, wherein the chlorination of acetoacetic acid monomethylamide is performed in the presence of 0.3 to 1 mole of urea per mole of acetoacetic acid monomethylamide.

5. Process according to claim 1, wherein the chlorination of acetoacetic acid monomethylamide is performed in the presence of 0.6 to 0.8 mole of urea per mole of acetoacetic acid monomethylamide.

6. Process according to claim 1, wherein there is added to the reaction mixture, to avoid the formation of foam and crusts, 1 to 2% by weight of an organic solvent immiscible with water.

7. Process according to claim 1, wherein there is added to the reaction mixture, to avoid the formation of foam and crusts, 1 to 2% by weight of 1,2-dichloroethane, 1,1-dichloroethane, chloroform, carbon tetrachloride or methylene chloride.

8. Process according to claim 1, wherein there is added to the reaction mixture, to avoid the formation of foam and crusts, 1 to 2% by weight of 1,2-dichloroethane.

9. Process according to claim 1, wherein the starting reaction mixture contains 45 to 65% by weight of water, 15 to 25% by weight of acetoacetic acid monomethylamide, 8 to 20% by weight of a water-soluble alkali metal salt or ammonium salt, 8 to 10% by weight of urea and 1 to 2% by weight of an organic solvent immiscible with water.

10. Process according to claim 1, wherein the reaction mixture after chlorination is neutralised by the introduction of ammonia.

11. Process according to claim 1, wherein 50 to 85% of the mother liquor remaining after separation of the β-monochloroacetoacetic acid monomethylamide and the precipitated alkali metal salt or ammonium salt is recyclised back into the chlorination stage.

* * * * *